(12) United States Patent
Melloy et al.

(10) Patent No.: US 11,471,184 B2
(45) Date of Patent: Oct. 18, 2022

(54) ENDOVASCULAR CUTTING CATHETER AND RELATED METHOD

(71) Applicant: C.R. BARD, INC., Tempe, AZ (US)

(72) Inventors: Ryan Melloy, Fountain Hills, AZ (US); Cassandra Van Allen, Tempe, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/605,748

(22) PCT Filed: Apr. 30, 2019

(86) PCT No.: PCT/US2019/029942
§ 371 (c)(1),
(2) Date: Oct. 22, 2021

(87) PCT Pub. No.: WO2020/222808
PCT Pub. Date: Nov. 5, 2020

(65) Prior Publication Data
US 2022/0202440 A1    Jun. 30, 2022

(51) Int. Cl.
*A61B 17/3207* (2006.01)
*A61B 17/32* (2006.01)

(52) U.S. Cl.
CPC ........ *A61B 17/320783* (2013.01); *A61B 17/320725* (2013.01); *A61B 2017/320064* (2013.01); *A61B 2017/320791* (2013.01)

(58) Field of Classification Search
CPC ........ A61B 17/3207; A61B 17/320758; A61B 17/320787; A61B 17/320725; A61B 2017/320791; A61B 17/320064
See application file for complete search history.

(56) References Cited

U.S. PATENT DOCUMENTS

| | | |
|---|---|---|
| 5,697,944 A | 12/1997 | Lary |
| 5,800,450 A | 9/1998 | Lary |
| 6,283,951 B1 * | 9/2001 | Flaherty ............ A61M 25/0068 604/164.11 |

(Continued)

FOREIGN PATENT DOCUMENTS

| | | |
|---|---|---|
| DE | 3921071 A1 | 2/1991 |
| WO | 2017192941 A1 | 11/2017 |

*Primary Examiner* — Tuan V Nguyen
(74) *Attorney, Agent, or Firm* — Dickinson Wright PLLC; Andrew D. Dorisio

(57) ABSTRACT

An apparatus for treating a lesion in a vasculature has a catheter shaft (12) with a plurality of openings (16), which may be axially spaced. One or more cutters (18, 18') are adapted for moving from a retracted position to a deployed position projecting from one of the plurality of openings for cutting the lesion, such as by being biased toward the opening and retracting upon engaging a leading edge thereof when the support is advanced proximally. A shaft forming part of the catheter may include a plurality of lateral openings and a plurality of cutters. The cutter(s) may be attached to a support adapted for moving independently within the shaft from a first position in which the cutter(s) move to a deployed position to project from a corresponding one of the plurality of openings for cutting the lesion. Related methods are also disclosed.

13 Claims, 5 Drawing Sheets

(56) References Cited

U.S. PATENT DOCUMENTS

| | | | |
|---|---|---|---|
| 6,302,870 B1 * | 10/2001 | Jacobsen | A61B 17/22 |
| | | | 604/170.03 |
| 8,465,451 B2 * | 6/2013 | McRae | A61B 18/18 |
| | | | 604/93.01 |
| 8,945,060 B2 * | 2/2015 | Bunch | A61M 25/0084 |
| | | | 604/173 |
| 2004/0122457 A1 | 6/2004 | Weber | |
| 2004/0193196 A1 | 9/2004 | Appling et al. | |
| 2010/0268175 A1 | 10/2010 | Lunsford et al. | |

* cited by examiner

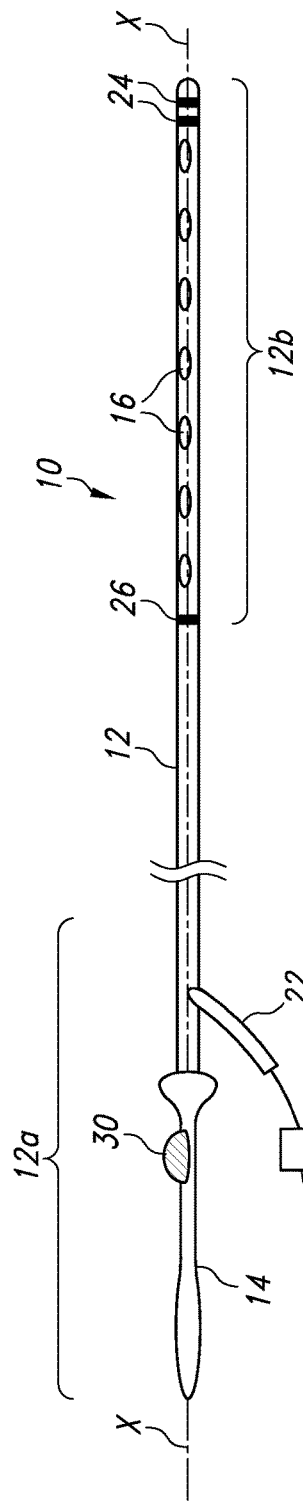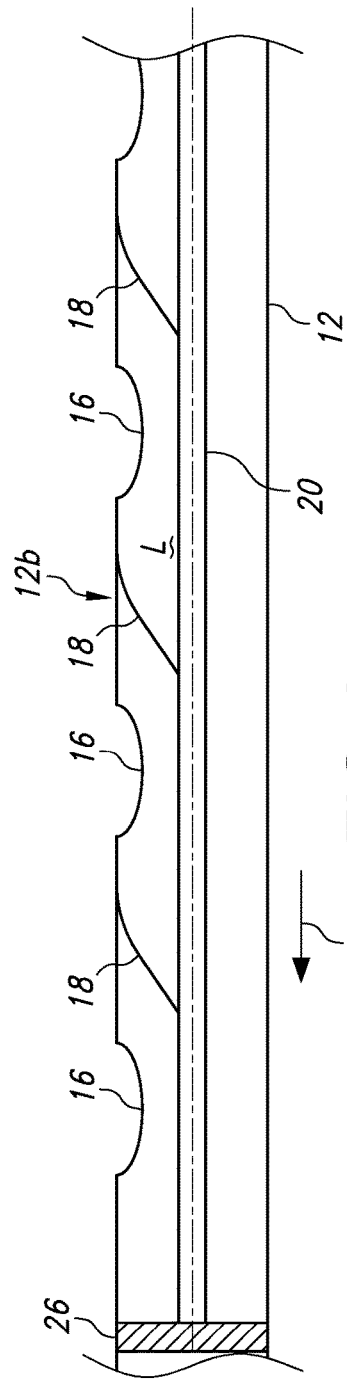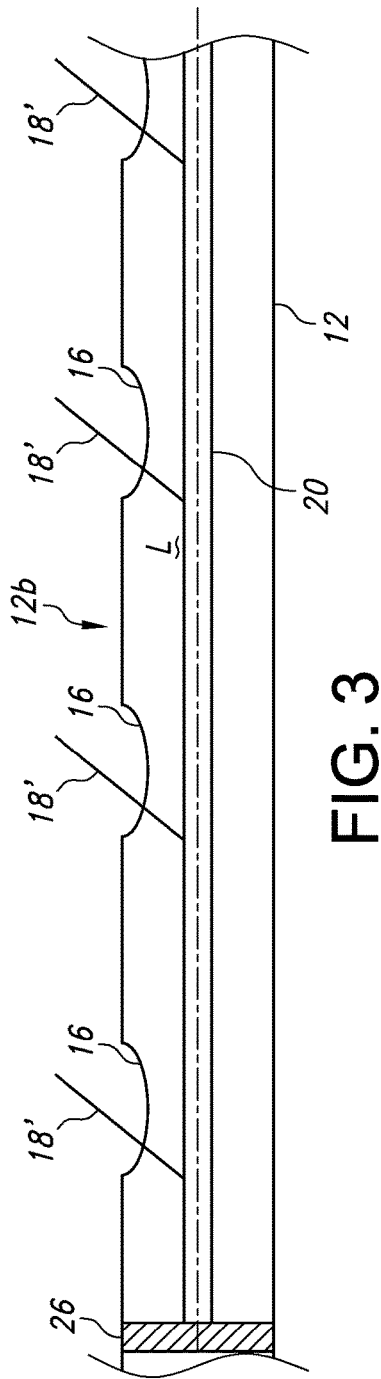

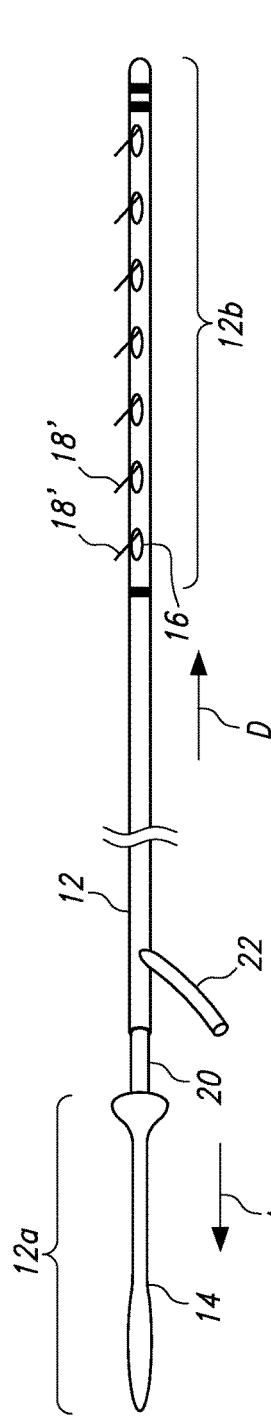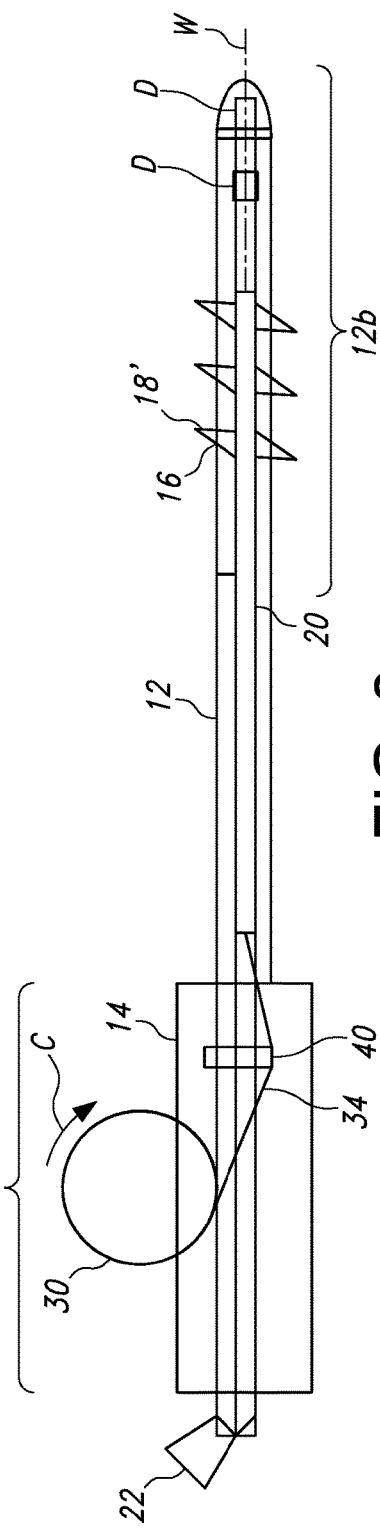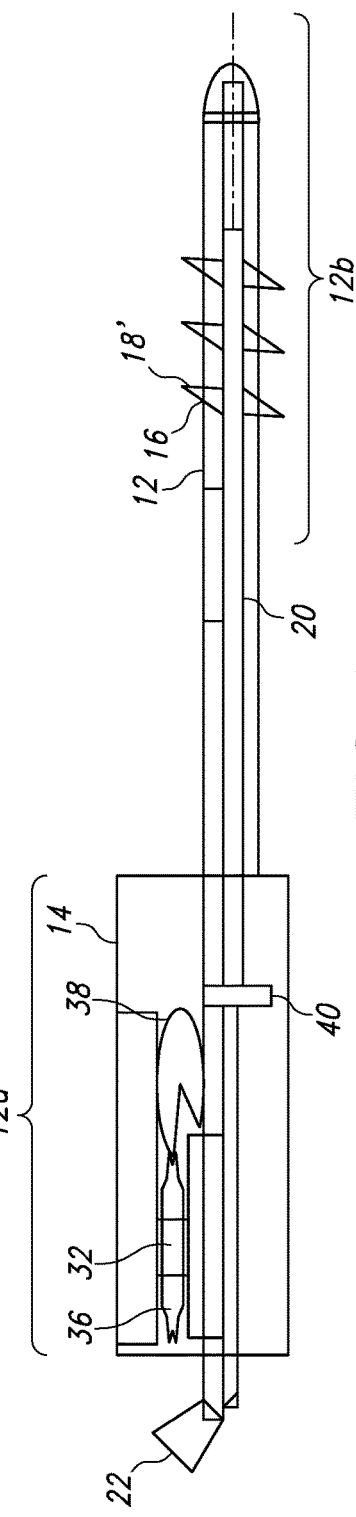
FIG. 7
FIG. 8
FIG. 9

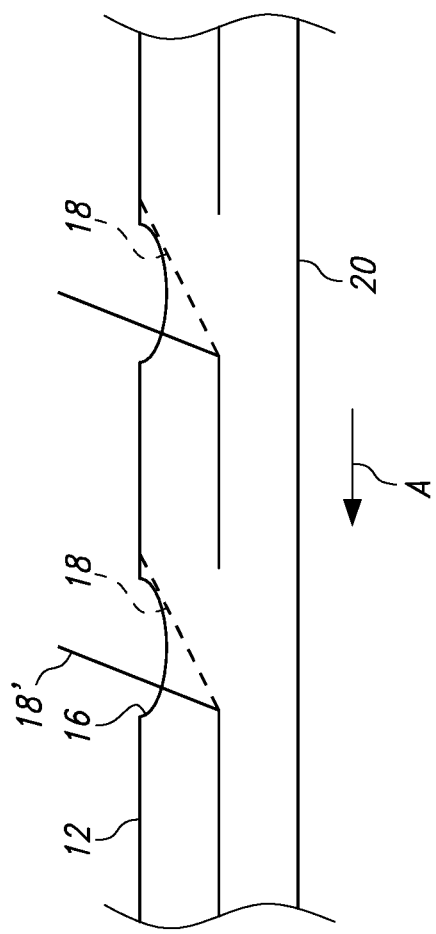
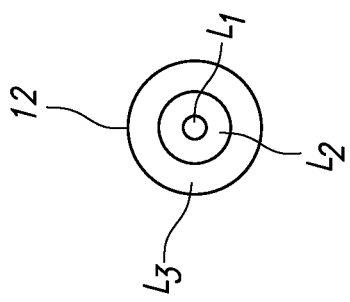

ENDOVASCULAR CUTTING CATHETER AND RELATED METHOD

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

This disclosure pertains to devices for providing endovascular treatment and, in particular, a catheter for cutting a vessel wall in a controlled manner, such as for slicing or scoring a lesion associated therewith.

BACKGROUND

Balloon dilatation catheters are used to treat lesions in vessels, such as by way of angioplasty. While successful for use in a variety of applications or locations in the vasculature, some situations call for a different approach in view of the possibility of "elastic recoil," which refers to the inherent resistance of a tissue to changes in shape, and the tendency of the tissue to revert to its original shape once deformed. Furthermore, some applications, and particularly those "below the knee" (BTK) involve hard calcifications, for which balloon angioplasty alone may be contraindicated. Moreover, the use of pharmacological agents to lesions for enhanced treatment may be desirable in some instances, and efficacy may be increased by actively cutting prior to application.

Accordingly, it would be desirable to provide a simple, yet effective apparatus for cutting a vessel wall and, in particular, for slicing or scoring a lesion associated therewith. Such a device would be readily useful in a variety of locations in the vasculature, including where particularly hard calcifications might be present, and conditions dictate a more reliable and effective approach than known proposals.

SUMMARY

An object of the invention is to provide an apparatus for endovascular cutting and, in particular, a cutter for cutting a vessel wall, (and more specifically, a lesion, plaque or other obstruction) that addresses and overcomes the foregoing limitations, and possibly others that have yet to be discovered.

According to one aspect of the disclosure, an apparatus for treating a lesion in a vasculature is provided. The apparatus comprises a catheter including a shaft including a plurality of lateral openings. A support within the shaft includes one or more cutters adapted for moving from a retracted position to a deployed position projecting radially from the shaft through one or more of the plurality of axially aligned lateral openings for cutting the lesion. The movement may be achieved in a variety of ways, including as a result of the cutters being biased toward the openings to project radially outwardly therefrom upon clearing a trailing edge thereof when advanced proximally by the associated support, and retracting upon engaging a leading edge thereof when the support is further advanced proximally.

In one embodiment, the support includes a plurality of cutters, each associated with one of the plurality of lateral openings, which may be axially aligned. The apparatus may further include an actuator for simultaneously actuating the plurality of cutters. In one particular embodiment, the actuator comprises a rotatable thumbwheel attached to the support, and may be adapted to retract the plurality of cutters from the deployed position. The actuator may instead comprise a handle for moving the support relative to the shaft.

The catheter may include an aspiration port, and a vacuum source may provide suction for drawing debris cut from the lesion by the one or more cutters when deployed. The plurality of cutters when deployed may project radially from the catheter in different directions. The plurality of lateral openings may comprise a first row of openings and a second row of openings spaced circumferentially from the first row of openings. At least one of the openings of the first row does not align circumferentially with at least one of the openings of the second row.

According to a further aspect of the disclosure, an apparatus for treating a lesion in a vasculature includes a catheter comprising a shaft including a plurality of lateral openings and a plurality of cutters. Each of the plurality of cutters is attached to a support adapted for moving within the shaft from a first position in which the plurality of cutters are retracted to a second position in which each of the plurality of cutters projects from a corresponding one of the plurality of openings for cutting the lesion.

In one embodiment, a first cutter projects from a first opening in the first position of the support, and the first cutter projects from a second opening proximal of the first opening in the second position of the support. The support may comprise a hypotube having the plurality of cutters formed therein. The plurality of lateral openings may comprise a first row of openings and a second row of openings spaced circumferentially about the shaft from the first row of openings. At least one of the openings of the first row may not align circumferentially with at least one of the openings of the second row.

Still a further aspect of the disclosure pertains to an apparatus for treating a lesion in a vasculature. The apparatus comprises a catheter comprising a shaft including a lateral opening and a cutter attached to a support and radially biased therefrom. The support is adapted for moving within the shaft to a first position in which the cutter projects from the lateral opening for cutting the lesion. In one embodiment, the shaft includes a plurality of lateral openings and a plurality of cutters, each for projecting from a corresponding one of the lateral openings in the first position of the shaft.

Yet another aspect of the disclosure is a method of treating a lesion in a vasculature. The method comprises providing a catheter comprising a shaft including a plurality of lateral openings and a support within the shaft supporting at least one cutter. The method further comprises deploying the cutter to project radially from the shaft through one of the plurality of openings for cutting the lesion.

In one embodiment, the moving step comprises moving a cutter through each of the plurality of openings. The method may further include the steps of: (1) retracting the cutter; and (2) deploying the cutter to project radially from the shaft through another of the plurality of openings. After the retracting step, the method may involve moving the catheter about the vasculature. The method may further include the step of disposing of the catheter after the deploying step, or applying suction to the catheter for drawing debris cut from the lesion by the cutter when deployed through the plurality of openings.

BRIEF DESCRIPTION OF THE DRAWING FIGURES

The above and further advantages of the invention according to the disclosure may be better understood by referring to the following description in conjunction with the accompanying drawings in which:

FIG. 1 illustrates one embodiment of a cutting catheter according to the disclosure;

FIG. 2 is an enlarged cutaway view of the FIG. 1 embodiment with the cutters retracted;

FIG. 3 is an enlarged cutaway view of the FIG. 1 embodiment with the cutters deployed;

Figure 4:
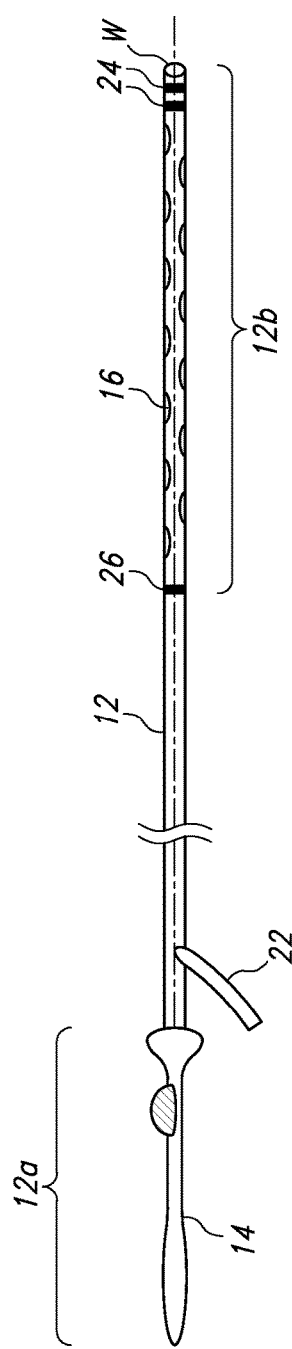
Figure 5:
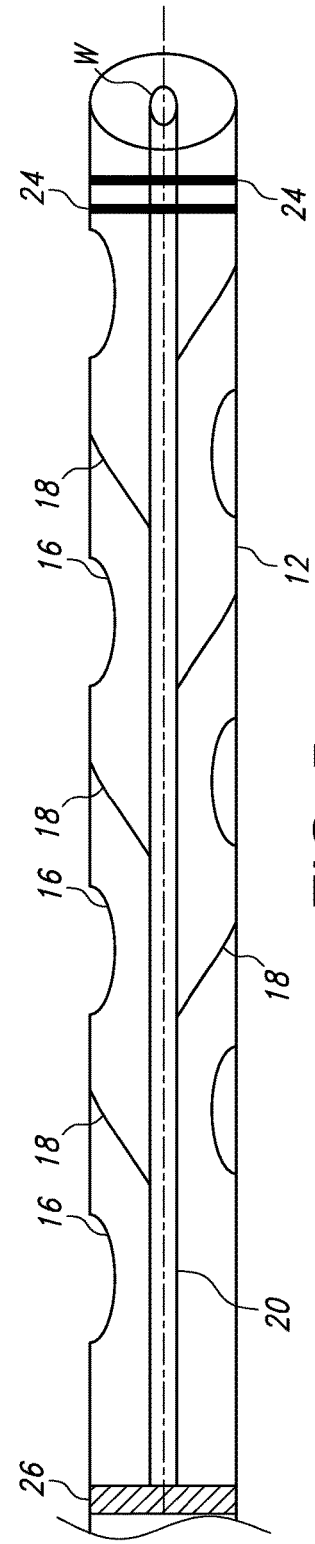
Figure 6:
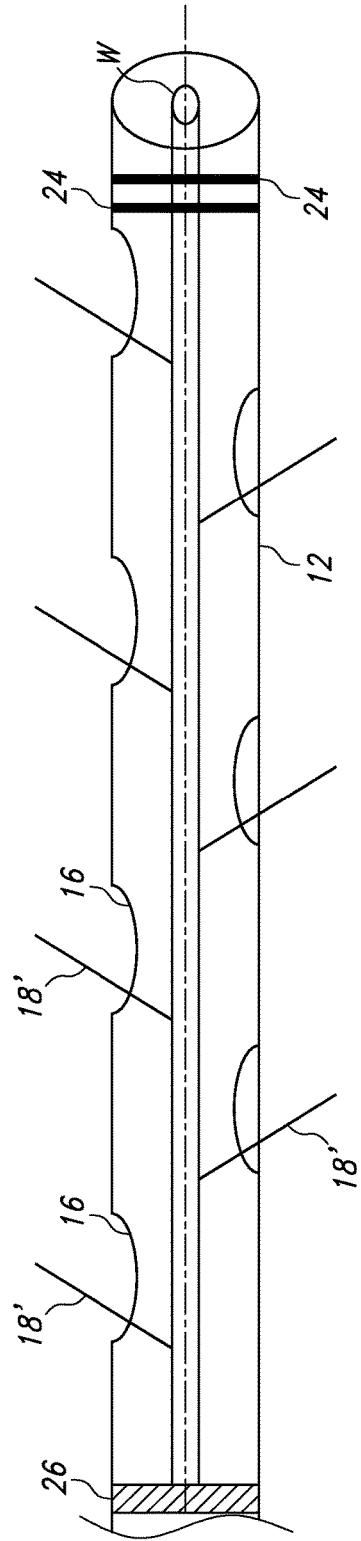

FIGS. 4, 5, and 6 are similar views of an alternative embodiment;

FIG. 7 illustrates one possible mode of actuation for the cutting catheter;

FIGS. 8 and 9 illustrate another possible mode of actuation for the cutting catheter;

FIG. 10 is a cutaway view of the manner in which the cutters are biased for deployment through the openings in the catheter shaft;

FIG. 11 illustrates an optional multi-lumen shaft; and

Figure 12:
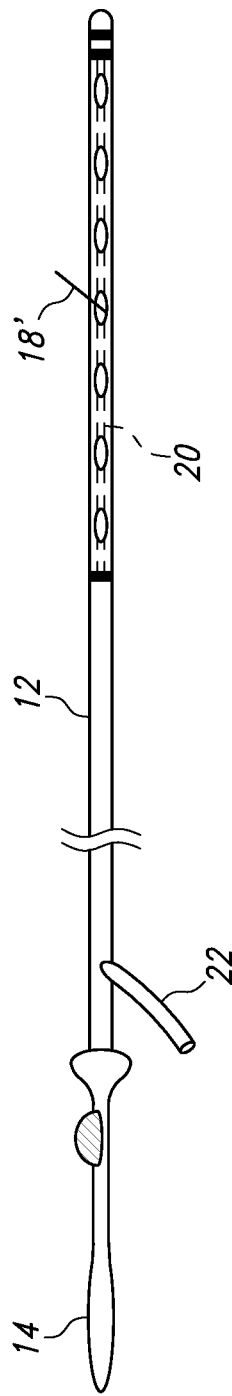
Figure 13:
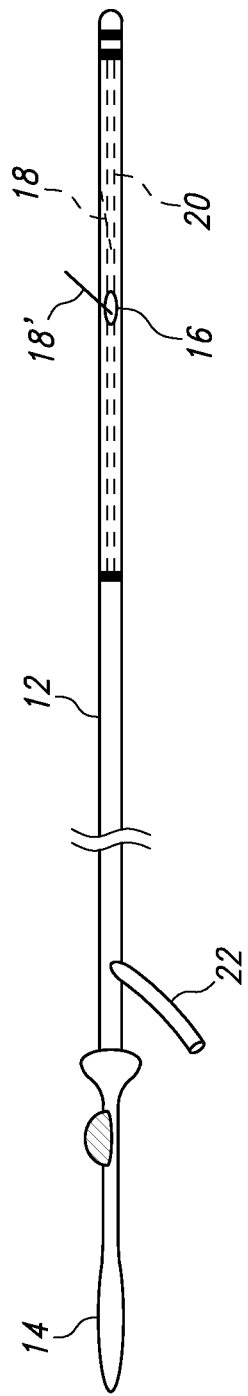

FIGS. 12 and 13 illustrate further embodiments of the cutting catheter according to the disclosure.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Referring first to FIG. 1, a cutting catheter 10 according to the disclosure is illustrated. The catheter 10 includes an elongated body or shaft 12 having a proximal end portion 12a with a handle 14 and a distal end portion 12b that may be adapted for cutting a vessel wall, as outlined further in the following discussion. While elongated along a longitudinal axis X and in a corresponding longitudinal direction, the shaft 12 is illustrated in a compact form simply for ease of illustration, and would normally have a considerable length (e.g., 50-150 centimeters, or otherwise suitable to allow the distal end portion 12b to reach a treatment area of interest in the vasculature while the proximal end portion 12a, and handle 14 in particular, remains accessible external to the vasculature).

According to one aspect of the disclosure, the catheter 10 is adapted for selectively slicing or scoring a location in the vasculature, such as a lesion on a vessel wall. With continued reference to FIG. 1, and also FIGS. 2 and 3, it can be appreciated that the distal end portion 12b of the shaft 12 includes a plurality of openings 16 through which one or more cutters 18 may project (reference numeral 18' FIG. 3) when deployed from a retracted position within the catheter 10 (FIG. 2). The openings 16 may be axially spaced, as shown. While seven openings are shown in the FIG. 1 embodiment, any number may be provided.

The cutters 18 may be attached to a common support 20 located within a lumen L of the shaft 12 and adapted for moving axially (arrow A) relative to the longitudinal axis as a result of actuation from outside the vasculature, as outlined further in the following discussion. Thus, when deployed and projecting radially outwardly through the openings 16, the cutters 18 are thus able to simultaneously slice or score adjacent portions of the vessel, such as a lesion connected thereto, via movement of the catheter 10 within a vessel. As a result of the alignment of the cutters 18 in the illustrated embodiment, the cutting may occur in a linear or aligned manner in the arrangement shown, but other alternatives are possible, as outlined further herein.

With continued reference to FIGS. 1-3, the shaft 12 may also include an aspiration port 22 along the proximal end portion 12a. This port 22 may be in fluid communication with the lumen L (which may comprise more than one lumen, as outlined further below; see also FIG. 11). Thus, suction applied to the port 22, such as from a vacuum source V, from a location external to the vasculature may be used to recover any material or debris dislodged as a result of the scoring or slicing action via openings 18.

Turning now to FIGS. 4-6, a second embodiment of a cutting catheter 10 is illustrated, which may have the same basic architecture as the first embodiment of FIGS. 1-3. However, as indicated the openings 16 in the shaft 12 are not linear, but rather spaced circumferentially and provided in two or more staggered rows. Thus, when the cutters 18 are deployed (FIG. 6) and the catheter 10 moved to and fro, it can be appreciated that the cutting action simultaneously occurs on plural sides of the shaft 12, and also in a manner that is staggered as a result of the positioning.

In any embodiment, the catheter 10 may be provided with one or more markers to indicate positioning within the vasculature from external to the body. Thus, as indicated in FIGS. 1-6, one or more markers 24 in the form of bands formed of a radiopaque or echogenic material may be provided at a distal tip of the shaft 12, and one or more proximal markers 26 may be provided at a proximal end of the distal end portion 12b. These markers 24, 26 allow the clinician to assess the positioning of the distal end portion 12b and, in particular, the openings 16 prior to deploying the cutters 18 to ensure the desired treatment effect may be achieved.

Actuation of the cutters 18 may be achieved by moving or retracting the support 20 in a proximal direction. Thus, as shown in FIG. 7, the handle 14 may be connected to the support 20, and pulled proximally (arrow A) relative to the shaft 12 in order to cause the cutters 18 to assume the deployed position, as shown. Pushing the handle 14 in the distal direction (arrow D) then causes the cutters 18 to assume the retracted position (see FIG. 2).

An example of an actuator for actuating the cutters 18 without the need for moving the handle 14 (which may be attached to shaft 12 at a proximal end thereof) is shown schematically in FIGS. 8 and 9. The handle 14 may include a rotatable wheel 30 (shown also in FIGS. 1 and 4, but optional in view of the foregoing discussion) projecting at least partially therefrom and arranged for being rotated in a clockwise direction C, such as by being mounted on a post 32. The wheel 30 is attached to a connector, such as a flexible wire 34, which is connected to a proximal end of the support 20, and thus pulls it proximally as a result of the clockwise rotation of the wheel 30. A gear 36 may also be provided on the post 32, and may engage a pawl 38, to ensure that only rotation in the clockwise direction C is possible.

Referring now to FIG. 10, the cutters 18 in one embodiment may be cut into a support 20 in the form of a thin walled metal hypotube, arranged to be normally biased in a radially outward direction so as to engage the interior of the shaft 12 (specifically, a surface of an inner wall thereof). As the support 20 is moved proximally as a result of the above-described rotation of the wheel 30, the cutters 18 are thus moved proximally as well until a corresponding opening 16 is reached, at which point the cutter may upon reaching a distal edge thereof spring radially outwardly from the shaft 12 for engaging a targeted material to be cut (compare position of cutter 18 in phantom and cutter 18' as a result of axial movement A). Continued movement in the proximal direction then forces the retraction of the cutters 18, such as upon engaging the proximal edge of the opening 16. Rather than via engagement with the shaft 12 as a result of inherent biasing, it is also possible to provide independently movable cutters connected to the support 20, which cutters may use ratchets or other mechanical locking devices, or may comprise shape memory materials (e.g., Nitinol) in order to cause the cutters 18 to radially project from the respective opening(s) 16 for scoring or slicing a lesion.

As can be appreciated, continued movement of the support 20 proximally by continued clockwise rotation of the wheel 30 causes the cutters 18 to reengage the proximal ends of the shaft 12 adjacent to the opening 16, and thus be biased toward a retracted position. Once the cutters 18 are fully retracted (which may be indicated by an index on the handle 14 associated with the wheel 30), the catheter 10 may then be moved throughout the vessel without causing scoring or slicing, such as for removal or to the location of another lesion or treatment area. At that location, the wheel 30 may be rotated to pull the support 20 proximally, and thus cause the cutters 18 to project from the next-adjacent aperture in a proximal direction. This may be repeated as necessary or desired until the support 20 engages a stop 40 (corresponding to retraction of the cutters 18, which as can be appreciated is desirable for withdrawal from the vasculature), at which point the catheter 10 is spent and may be discarded.

FIG. 11 illustrates that the shaft 12 may include multiple lumens. For instance, an innermost lumen $L_1$ may receive a guidewire W (see FIG. 8) for guiding the catheter 10 to a location in the vasculature for treatment (which may be an "over the wire" arrangement, or instead may be a "rapid exchange" type of arrangement, in which case distal ports P may be provided for receiving the guidewire), and may also extend through the handle 14 or other proximal end structure (e.g., a conventional hub). A second, outer lumen $L_2$ may be provided for receiving the support 20, and a third outer lumen $L_3$ may be provided in fluid communication with the aspiration port 22. However, it is possible to provide the arrangement with more or fewer lumens, as necessary or desired.

Referring to FIGS. 12 and 13, additional options for possible application to any disclosed embodiment are illustrated. FIG. 12 shows that only a single cutter 18' (shown actuated) may be provided on the support 20 (shown in phantom), but the shaft 12 may include a plurality of peripheral openings 16, as shown. Movement of the support 20, such as in proximal direction as described above, may thus cause the single cutter 18' once erected to collapse until it reaches the next-adjacent proximal opening and projects therefrom. In other words, the shaft 12 may include a plurality of openings 16 for associating with only a single cutter 18, depending on its positioning.

Likewise, the shaft 12 may include only a single opening 16, as shown in FIG. 13, from which a cutter may radially project (18'). However, the shaft (not shown) may be provided with plural cutters 18 (see FIG. 10), such that proximal movement causes the deployed cutter to collapse and eventually a next-adjacent distal cutter (shown in phantom) to reach the opening and project therefrom. In this manner, a fresh cutter may be used for each slicing or scoring event.

Each cutter 18 may comprise a sharpened tip and/or a thin, blade edge of various shapes (flat, convex, chiseled, single bevel, double bevel, etc.) to provide a precision cut. The blade edge may also be serrated (single or double), scalloped, chamfered, wavy, or take other shapes or forms, depending on the particular use, and more than one blade edge may be provided (such as on both a distal and a proximal side also on lateral sides thereof). While the cutters 18 are shown normally projecting in a distal direction, it can be appreciated that the cutters 18 may project in the proximal direction as well, and be made to collapse upon engaging the proximal end of the opening 16 (either as a result of flexing, or a suitable mechanical connection with the shaft 20.

In summary, a cutting catheter 10 for cutting a vessel wall and for scoring or slicing a lesion in a vessel, is provided. The catheter 10 includes a shaft 12 with one or more openings 16 for receiving one or more cutters 18 associated with a support 20 adapted for translating within the shaft. When deployed, the catheter 10 may thus actively score or slice a lesion simultaneously with the one or more cutters 18, which may be linearly arranged or circumferentially spaced (and possibly in staggered rows). The cutter(s) 18 may also be retracted, the catheter 10 moved about a vessel, and then redeployed for scoring or slicing a different location.

This disclosure may be considered to relate to the following items:

1. An apparatus for treating a lesion in a vasculature, comprising:
a catheter comprising a shaft including a plurality of axially aligned lateral openings and a support within the shaft including one or more cutters adapted for moving from a retracted position to a deployed position (such as by being biased along an interior of the shaft and then-projecting radially from the shaft through one or more of the plurality of axially aligned lateral openings for cutting the lesion).
2. The apparatus of item 1, wherein the support includes a plurality of cutters, each associated with one of the plurality of axially aligned lateral openings.
3. The apparatus of item 2, further including an actuator for simultaneously actuating the plurality of cutters.
4. The apparatus of item 3, wherein the actuator comprises a rotatable thumbwheel attached to the support.
5. The apparatus of item 3, wherein the actuator is adapted to retract the plurality of cutters from the deployed position.
6. The apparatus of item 3, wherein the actuator comprises a handle for moving the support relative to the shaft.
7. The apparatus of any of items 1-6, further including a vacuum source for drawing debris cut from the lesion by the one or more cutters when deployed.
8. The apparatus of any of items 2-7, wherein the plurality of cutters when deployed project radially from the catheter in different directions.

9. The apparatus of any of items 2-8, wherein the plurality of openings comprise a first row of openings and a second row of openings spaced circumferentially from the first row of openings.

10. The apparatus of any of items 2-9, wherein at least one of the openings of the first row does not align circumferentially with at least one of the openings of the second row.

11. An apparatus for treating a lesion in a vasculature, comprising:

a catheter comprising a shaft including a plurality of lateral openings and a plurality of cutters, each of the plurality of cutters attached to a support adapted for moving within the shaft from a first position in which the plurality of cutters are retracted to a second position in which each of the plurality of cutters projects from a corresponding one of the plurality of openings for cutting the lesion.

12. The apparatus of item 11, wherein a first cutter projects from a first opening in the first position of the support, and the first cutter projects from a second opening proximal of the first opening in the second position of the support.

13. The apparatus of any of items 1-12, wherein the support comprises a hypotube having the plurality of cutters formed therein.

14. The apparatus of any of items 11-13, wherein the plurality of lateral openings comprise a first row of openings and a second row of openings spaced circumferentially about the shaft from the first row of openings.

15. The apparatus of item 14, wherein at least one of the openings of the first row does not align circumferentially with at least one of the openings of the second row.

16. An apparatus for treating a lesion in a vasculature, comprising:

a catheter comprising a shaft including a lateral opening and a cutter attached to a support and biased radially outwardly therefrom, the support adapted for moving within the shaft to a first position in which the cutter projects from the lateral opening for cutting the lesion.

17. The apparatus of item 16, wherein the shaft includes a plurality of lateral openings and a plurality of cutters, each for projecting from a corresponding one of the lateral openings in the first position of the shaft.

18. A method of treating a lesion in a vasculature, comprising:

providing a catheter comprising a shaft including a plurality of lateral openings and a support within the shaft supporting at least one cutter; and deploying the cutter to project radially outwardly from the shaft through one of the plurality of openings for cutting the lesion.

19. The method of item 18, wherein the moving step comprises moving a cutter through each of the plurality of openings.

20. The method of item 17 or item 18, further including the step of:

retracting the cutter; and deploying the cutter to project radially from the shaft through another of the plurality of openings.

21. The method of item 20, further including, after the retracting step, moving the catheter about the vasculature.

22. The method of any of items 17-21, further including the step of disposing of the catheter after the deploying step.

23. The method of any of items 17-22, further including the step of applying suction to the catheter for drawing debris cut from the lesion by the cutter when deployed through the plurality of openings.

Each of the following terms written in singular grammatical form: "a", "an", and the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of" and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or subprocedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or subprocedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refer to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

The invention claimed is:

1. An apparatus for treating a lesion in a vasculature, comprising:
a catheter comprising a shaft including a plurality of lateral openings and a support within the shaft including one or more sharpened cutters adapted for moving from a retracted position to a deployed position projecting radially from the shaft through one or more of the plurality of axially aligned lateral openings for cutting the lesion, and wherein the catheter comprises an aspiration port in fluid communication with the plurality of lateral openings for communicating with a vacuum source for drawing debris cut from the lesion by the one or more cutters when deployed.

2. The apparatus of claim 1, wherein the one or more sharpened cutters of the support comprises a plurality of sharpened cutters, each associated with one of the plurality of axially aligned lateral openings.

3. The apparatus of claim 2, further including an actuator for simultaneously actuating the plurality of cutters.

4. The apparatus of claim 3, wherein the actuator comprises a rotatable thumbwheel attached to the support.

5. The apparatus of claim 3, wherein the actuator is adapted to retract the plurality of cutters from the deployed position.

6. The apparatus of claim 3, wherein the actuator comprises a handle for moving the support relative to the shaft.

7. The apparatus of claim 2, wherein the plurality of cutters when deployed project radially from the catheter in different directions.

8. The apparatus of claim 1, wherein the plurality of lateral openings comprise a first row of openings and a second row of openings spaced circumferentially from the first row of openings.

9. The apparatus of claim 8, wherein at least one of the openings of the first row does not align circumferentially with at least one of the openings of the second row.

10. An apparatus for treating a lesion in a vasculature, comprising:
a catheter comprising a shaft including a plurality of lateral, axially spaced openings and a plurality of sharpened cutters, each of the plurality of cutters attached to a support adapted for moving within the shaft from a first position in which the plurality of cutters are retracted to a second position in which each of the plurality of cutters projects from a corresponding one of the plurality of openings for cutting the lesion, and wherein a first cutter of the plurality of sharpened cutters projects from a first opening in the first position of the support, and the first cutter projects from a second opening proximal of the first opening in the second position of the support.

11. The apparatus of claim 10, wherein the support comprises a hypotube having the plurality of cutters formed therein.

12. The apparatus of claim 10, wherein the plurality of lateral openings comprise a first row of openings and a second row of openings spaced circumferentially about the shaft from the first row of openings.

13. The apparatus of claim 12, wherein at least one of the openings of the first row does not align circumferentially with at least one of the openings of the second row.

* * * * *